United States Patent [19]

Chabrand et al.

[11] Patent Number: 5,714,425
[45] Date of Patent: Feb. 3, 1998

[54] CATALYST COMPOSITIONS AND PROCESS FOR PREPARING POLYOLEFINS

[75] Inventors: Christine Jacqueline Chabrand, Martigues, France; Ian Raymond Little, Middlesex; John Paul McNally, Berkshire, both of United Kingdom

[73] Assignee: BP Chemicals Limited, London, England

[21] Appl. No.: 513,663

[22] Filed: Aug. 10, 1995

Related U.S. Application Data

[63] Continuation of Ser. No. 467,079, Jun. 6, 1995, abandoned, which is a continuation of Ser. No. 112,098, Aug. 26, 1993, abandoned.

[30] Foreign Application Priority Data

Sep. 4, 1992 [GB] United Kingdom ............... 92 18805.1
Mar. 23, 1993 [GB] United Kingdom ............... 93 05963.2

[51] Int. Cl.$^6$ .................... B01J 31/00; C07F 7/28; C07F 17/00; C07F 17/02
[52] U.S. Cl. ................ 502/117; 502/103; 502/152; 502/158; 556/52; 556/53; 556/56; 526/160; 526/943; 987/2
[58] Field of Search ................ 556/52, 53, 56; 526/943, 160; 987/2; 502/103, 117, 152, 158

[56] References Cited

U.S. PATENT DOCUMENTS

| | | |
|---|---|---|
| 4,363,904 | 12/1982 | Fraser . |
| 5,145,819 | 9/1992 | Winter et al. ............... 502/117 |
| 5,308,817 | 5/1994 | Reddy et al. ............... 502/117 |
| 5,374,752 | 12/1994 | Winter et al. ............... 502/154 |
| 5,455,365 | 10/1995 | Winter et al. ............... 502/117 |

FOREIGN PATENT DOCUMENTS

| | | |
|---|---|---|
| 0298700 | 1/1989 | European Pat. Off. . |
| 0372414 | 6/1990 | European Pat. Off. . |
| 0459142 | 12/1991 | European Pat. Off. . |
| 0496193 | 7/1992 | European Pat. Off. . |
| 2680794 | 3/1993 | France . |
| 8702991 | 5/1987 | WIPO . |

*Primary Examiner*—Elizabeth D. Wood
*Attorney, Agent, or Firm*—Brooks Haidt Haffner & Delahunty

[57] ABSTRACT

Catalyst compositions comprising metallocene complexes having polymerisable olefinic groups substituent on an organic group containing a cyclopentadienyl nucleus may be used for the preparation of polyolefins. The catalyst compositions may be in the form of polymers comprising the metallocene complex and may be suitably supported on inorganic supports. Polymers having a broad range of density and melt indices as well as low hexane extractables and excellent powder morphology and flowability may be obtained by use of the catalyst compositions. Preferred metallocene complexes are zirconium complexes in which the polymerisable olefinic group is vinyl.

15 Claims, 2 Drawing Sheets

CATALYST COMPOSITIONS AND PROCESS FOR PREPARING POLYOLEFINS

This application is a continuation of application Ser. No. 08/467,079 filed on Jun. 6, 1995 and now abandoned which, in turn, is a continuation of application Ser. No. 08/112,098 filed on Aug. 26, 1993 now abandoned.

The present invention relates to novel catalyst compositions comprising metallocene complexes and their use in the polymerisation of olefins.

BACKGROUND OF THE INVENTION

Metallocene complexes of Group IVA metals such as (cyclopentadienyl)$_2$ZrCl$_2$ are known as homogeneous polyolefin catalysts in the presence of a suitable co-catalyst. Such catalyst systems have proven to be highly active towards ethylene and alpha olefins forming narrow molecular weight distributions of polyolefins.

It would be highly desirable to provide catalysts which may be used, particularly in the gas phase, to prepare polymers which show good performance and processability.

We have now discovered that catalyst compositions comprising metallocene complexes having a polymerisable group may advantageously be used in the polymerisation of olefins.

SUMMARY OF THE INVENTION

Accordingly, the present invention provides a catalyst composition comprising at least one metallocene complex of general formula I or II

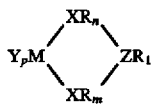
(II)

wherein R is a univalent or divalent 1-20C hydrocarbyl, or a 1-20C hydrocarbyl containing substituent oxygen, silicon, phosphorus, nitrogen or boron atoms with the proviso that at least one R group contains a polymerisable group and preferably contains at least three carbon atoms, and when there are two R groups present they may be the same or different, and when R is divalent it is directly attached to M, and replaces a Y ligand, wherein X is an organic group containing a cyclopentadienyl nucleus, M is a Group IVA metal, Y is a univalent anionic ligand, and for formula I, n is an integer of 1 to 10 x is either 1 or 2, and when x=1, p=0-3, that is, when all R are univalent, p=3; when one R is divalent, p=2, when two Rs are divalent, p=1 and when three Rs are divalent, p=0, when x=2, p=0-2, that is, when all R are univalent, p=2; when one R is divalent, p=1 and when two Rs are divalent, p=0, and for formula II, n, m and l are integers or 0 such that n+m+l ≧ 1, p=0-2, that is, when all R are univalent, p=2; when one R is divalent, p=1 and when two Rs are divalent, p=0, and Z is a C$_1$ to C$_4$ alkylene radical or a dialkyl germanium or silicon or an alkyl phosphine or amine radical or bis-dialkylsilyl or bis-dialkylgermanyl containing hydrocarbyl groups having 1 to 4 carbon atoms bridging the cyclopentadienyl nuclei.

DETAILED DESCRIPTION OF THE INVENTION AND THE PREFERRED EMBODIMENTS

The metallocene complex of the present invention is a Group IVA metallocene complex of general formula I or II wherein M is suitably hafnium, zirconium or titanium. Preferably, M is zirconium.

In the metallocene complex of general formula I or II, X comprises a cyclopentadienyl nucleus. Suitably X represents a single ring cyclopentadienyl nucleus or a fused ring one such as indenyl or tetrahydroindenyl or fluorenyl nucleus. Preferably X is a single ring cyclopentadienyl nucleus.

In the metallocene complex of general formula I or II when there are two or more R groups present these may be the same or may be different. At least one of R contains the polymerisable group, especially an olefinic group.

The R groups of the metallocene complex are independently organic hydrocarbyl groups, at least one of the R groups having a polymerisable group. For the purposes of the present invention, a polymerisable group may be defined as a group which can be incorporated into a growing polymer chain. The preferred polymerisable group of which R consists or comprises is an olefinic group. Preferably, the olefinic group consists of or comprises a vinyl group.

R may independently be an alkenyl group of suitably 2 to 20, preferably 3-8 carbon atoms. The alkenyl may suitably be linear or branched, for example, an alkenyl group such as but-3-enyl or oct-7-enyl; or an alkenyl aryl, alkenyl cycloalkyl or alkenyl aralkyl group, each having 8 to 20 carbon atoms, especially p-vinyl phenyl or p-vinyl benzyl.

Additionally, one of the R groups may be a silyl group such as trimethyl silyl, triethyl silyl, ethyldimethyl silyl, methyldiethyl silyl, phenyldimethyl silyl, methyldiphenyl silyl or triphenyl silyl R may also represent an organic hydrocarbyl group such as an alkyl group of 1 to 10 carbon atoms such as methyl, ethyl, propyl hydrocarbyl groups or a cycloalkyl group containing 5 to 7 carbon atoms, for example, cyclohexyl or an aromatic or aralkyl group of 6 to 20 or 7 to 20 carbon atoms respectively, for example, phenyl or benzyl.

m and/or n is at least 1 and not greater than 10, e.g. 1–5, the maximum value depending on the number of possible substituent positions available in the X nucleus. Where for example X is cyclopentadienyl, the maximum for n is 5 whilst the maximum of n is 7 for the indenyl nucleus.

Y is a univalent anionic ligand. Suitably the ligand is selected from hydride, halides, for example, chloride and bromide, substituted hydrocarbyls, unsubstituted hydrocarbyls, alkoxides, amides or phosphides, for example, a dialkylamide or a dialkyl or alkyl aryl phosphide group with 1 to 10 carbon atoms in each alkoxide or alkyl group and 6 to 20 carbons in the aryl group.

The preferred metallocene complex of general formula I is when:

M is zirconium

R is C$_3$ to C$_{10}$ hydrocarbyl having a vinyl group

X is a cyclopentadienyl group

Y is chloride, n is 1 or 5 x is 2, and p is 2.

The preferred metallocene complex of general formula II is when:

M is zirconium

R is C$_3$ to C$_{10}$ hydrocarbyl with a vinyl group

X is an indenyl group

Y is chloride n=m=1 l=0, and

Z is a $C_1$ to $C_4$ alkylene or a bis dimethylsilyl containing $C_1$ to $C_4$ hydrocarbyl group.

DESCRIPTION OF THE DRAWINGS

Examples of suitable metallocene complexes of general formula I and general formula II are illustrated in the attached FIGS. 1 and 2 respectively.

DETAILED DESCRIPTION OF THE INVENTION AND PREFERRED EMBODIMENTS

Figure 1:
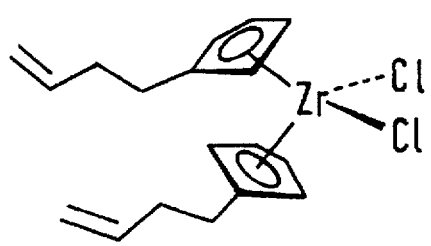
Figure 1:
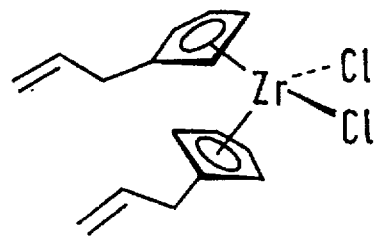
Figure 1:
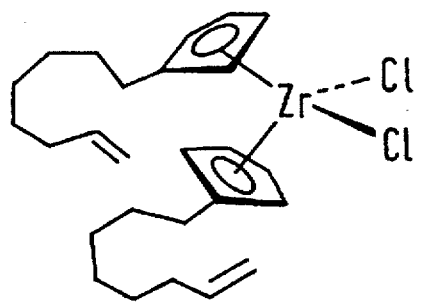
Figure 1:
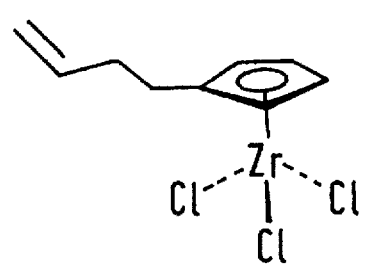
Figure 1:
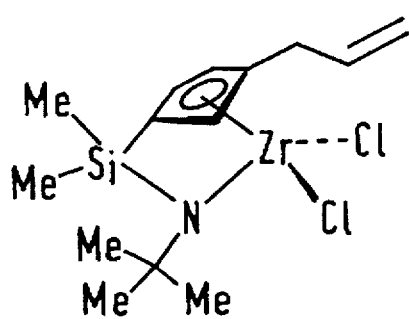
Figure 1:
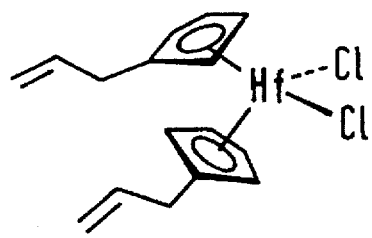
Figure 1:
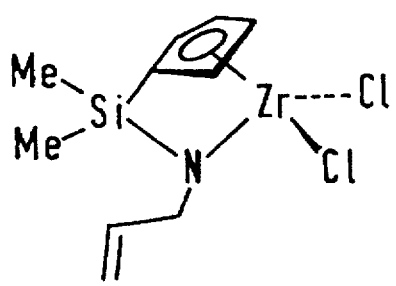
Figure 1:
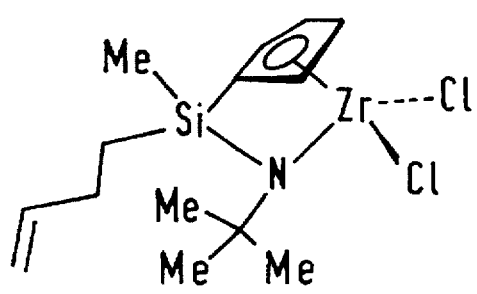
Figure 2:
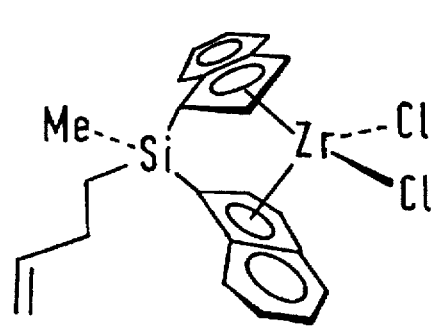
Figure 2:
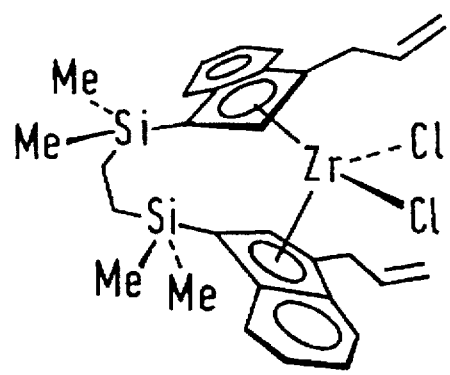
Figure 2:
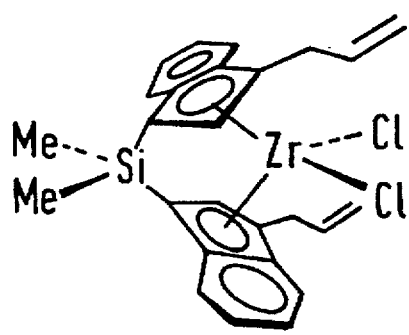
Figure 2:
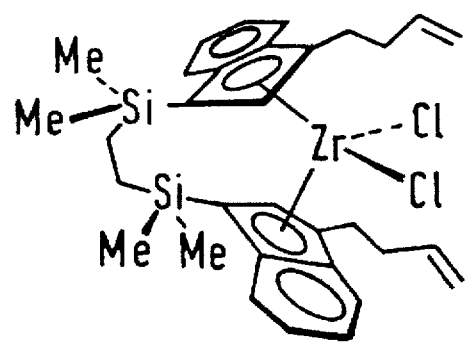
Figure 2:
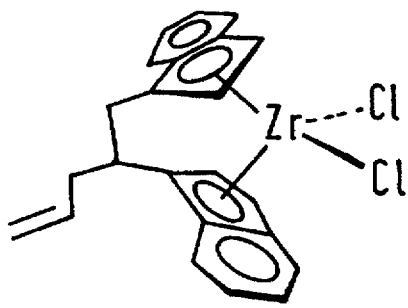
Figure 2:
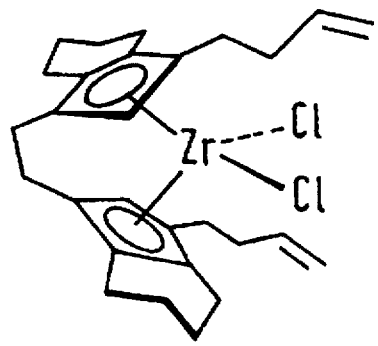

Metallocene complexes of general formula I, where x=2, and general formula II may suitably be prepared by reacting a suitable group IVA metal salt of the general formula $MYYCl_2$ with a compound with a polymerisable group containing a cyclopentadienyl anion of the general formula $[(R)_nX]M'$ or $[R_nX-ZR_l-XR_m]M'_2$. Suitably the M' is an alkaline metal. It is preferred that the Group IV metal salt is a tetra halide salt, most preferably a tetrachloride salt. It is preferred that the preparation of the metallocene complex is carried out in the presence of an anhydrous organic solvent such as an aliphatic ether such as diethyl ether or an aromatic hydrocarbon such as toluene or a cyclic ether such as tetrahydrofuran and under an inert atmosphere. The preferred conditions are in the presence of dry tetrahydrofuran and under dry nitrogen.

If a metallocene complex is to be prepared in which the R groups are different then for formula (I) where x=2 two different $[(R)_nX]M'$ compounds are used and for formula II, the appropriate mixed compound is used.

The salt of general formula $[(R)_nX]M'$ (III) may be prepared by any suitable method from the corresponding compound of formula $(R)_nXH$ (IV) by reaction with a suitable metal. Suitably, the metal is an alkaline metal selected from lithium, sodium or potassium. The metal may also be an organo hydrocarbyl alkali metal compound such as an alkyl or phenyl sodium, lithium or potassium compound. Preferably, it is a lithium compound.

The compound $(R)_nXH$ may itself be formed by reaction of a compound of general formula XM" (V) where M" is an alkali metal. Suitably XM" is sodium cyclopentadiene. XM" may be reacted with a compound R—R" where R is as defined above and R" is a suitable leaving group. Alternatively, XM" and X'M" may be reacted with Z(R)$_l$R"$_2$. R" may suitably be a nucleophilic leaving group. Preferably, R" is a halide selected from chloride, bromide or iodide, an ester group, especially a sulphonate ester such as alkane sulphonate or aryl sulphonate. Suitably, the aforementioned reactions are carried out in the presence of an anhydrous organic solvent and under an inert atmosphere.

Where it is desired to prepare the metallocene complex of general formula I wherein x is 1, the complex may suitably be prepared using procedures well known in the field. For example, the cyclopentadiene compound $X(R)_nH$ could be reacted with a metallating agent where the metal (M") is a Group I alkali metal to provide $X(R)_nM"$. Metallating agents include n-BuLi or MeLi. Suitably $X(R)_nM"$ is then reacted with trimethylsilyl chloride in an appropriate solvent to provide $(Me_3Si)X(R)_n$. Further reaction with a Group IV metal halide will suitably provide a metallocene complex of general formula $M[X(R)_n]Y_3$. This synthesis is particularly preferred for the preparation of the titanium metallocene, although variations of the synthesis can be used to prepare analogous zirconium and hafnium complexes. In another example, if $X(R)_n$ contains one or more functional groups with a protonated heteroatom, additional equivalents of the metallating reagent will deprotonate both the cyclopentadiene nucleus and one or more of the heteroatoms. Reaction of the metallated polyanion with a Group IV metal halide will suitably provide a metallocene complex of general formula $M[X(R)_n]Y_t$, where Y is halide and t=0–2. In this case, (3–t) R groups will bridge the cylopentadienyl nucleus and the metal atom by means of a bond between the metal atom and a deprotonated heteroatom.

If desired the complexes of formula I or II wherein Y is halide may be converted into the complexes of formula I or II wherein Y is the other specified groups by reaction of the halide with an appropriate nucleophile e.g. alkoxide.

One or more metallocene complexes of general formula I or II may suitably be used as a catalyst in various reactions. The complexes may suitably be supported on an inorganic support to give a supported catalyst composition which forms one aspect of the present invention. Any suitable inorganic support may be used, for example, inorganic oxides such as silica, alumina, silica-alumina mixtures, thoria, zirconia, magnesia, titania and mixtures thereof. Equally suitably inorganic halides may be used. Suitable halides include group IIA halides, e.g. magnesium chloride. The complex of formula I or II preferably comprises 0.01–50% by weight of said supported catalyst composition.

One or more metallocene complexes may suitably be impregnated onto the support material under anhydrous conditions and under an inert atmosphere. The solvent may then be evaporated under reduced pressure. The impregnated support may then be heated to remove any remaining solvent.

The metallocene complex of general formula I or II may be used in the presence of a suitable co-catalyst. Suitably the co-catalyst is an organometallic compound having a metal of Group IA, IIA, IIB or IIIB of the periodic table. Preferably, the metals are selected from the group including lithium, aluminium, magnesium, zinc and boron. Such co-catalysts are known for their use in polymerisation reactions, especially the polymerisation of olefins, and include organo aluminium compounds such as trialkyl, alkyl hydrido, alkyl halo and alkyl alkoxy aluminium compounds. Suitably each alkyl or alkoxy group contains 1 to 16 carbons. Examples of such compounds include trimethyl aluminium, triethyl aluminium, diethyl aluminium hydride, triisobutyl aluminium, tridecyl aluminium, tridodecyl aluminium, diethyl aluminium methoxide, diethyl aluminium ethoxide, diethyl aluminium phenoxide, diethyl aluminium chloride, ethyl aluminium dichloride, methyl diethoxy aluminium and methyl aluminoxane. The preferred compounds are alkyl aluminoxanes, the alkyl group having 1 to 10 carbon atoms, especially methyl aluminoxane. Where Y in the general formula I or II is independently hydrogen or hydrocarbyl, suitable co-catalysts also include Bronsted or Lewis acids.

The co-catalyst may be mixed with the metallocene, optionally on an inorganic support. Alternatively, the co-catalyst may be added to the polymerisation medium along with the metallocene complex. Suitably, the amount of co-catalyst mixed with metallocene complex may be such as to provide an atom ratio of M from the metallocene to the metal in the co-catalyst of 1–10,000:10,000–1 for aluminoxanes and 1–100:100–1 otherwise.

One or more metallocene complexes of general formula I or II, in the presence of a co-catalyst, may be used to produce polymers containing one or more metals M. The metallocene containing polymer usually contains a high group IVA metal content and is usually a low yield polyolefin, comprising one or more metallocene complexes of general formula I and/or II with one or more olefins.

Thus according to another aspect of the present invention there is provided a catalyst composition suitable for use in the polymerisation of olefins comprising a polymer containing a metallocene complex of general formula I or II as described above, preferably as a copolymer with at least one alpha-olefin and/or ethylene.

The metallocene containing polymer may suitably be prepared by heating one or more metallocene complexes of general formula I and/or II, optionally supported, usually in the presence of an inert solvent and/or suitable co-catalysts as described above and preferably in the presence of one or more alpha-olefins or ethylene, so that the metallocene complex is co-polymerised. Suitably the alpha-olefin may be a C3 to C10 olefin.

The conditions of formation of the metallocene containing polymer are substantially similar to those for the polymerisation of olefins described hereafter, but with a lower degree of polymerisation, e.g. for a shorter time.

The metallocene containing polymer may suitably be impregnated onto the support material under anhydrous conditions and under an inert atmosphere. The impregnation can be conducted using an inert solvent, in which case the solvent may then be evaporated under reduced pressure. The impregnated support may then be heated to remove any remaining solvent. Preferably, the metallocene containing polymer is dissolved in the inert solvent. Suitable inert solvents include aromatic hydrocarbons, such as toluene.

Any suitable inorganic support may be used for example, inorganic oxides such as silica, alumina. Equally suitable inorganic halides may be used. Suitable halides include Group IIA halides e.g. magnesium chloride.

The catalyst composition comprising the metallocene containing polymer may be used in the presence of a suitable co-catalyst, as described above. The co-catalyst may be mixed with the metallocene containing polymer optionally as an inorganic support. Alternatively the co-catalyst may be added to the polymerisation medium along with the metallocene containing polymer.

It is a particular advantage of this aspect of the present invention that an active catalyst composition comprising a metallocene containing polymer may be supported on an inorganic oxide or metal halide support without using cocatalysts such as aluminoxanes as the means of support. Aluminoxanes are expensive and difficult to handle and it is desirable to minimise their use. Conventionally, they are used as both a means of binding metallocenes to inorganic supports and as cocatalysts. The current invention obviates the need for aluminoxanes as a means of binding. This allows their use as cocatalysts only or not at all by selecting alternative cocatalysts, e.g. Bronsted or Lewis acids.

A further advantage of this aspect of the current invention is that it provides a support method which prevents desorption of metallocene complexes from a supported catalyst under certain polymerisation process conditions, e.g. slurry. Conventional metallocene support methods where the metallocene complex is simply adsorbed onto the support surface, with or without the use of cocatalysts such as aluminoxanes, may undergo some metallocene complex desorption under polymerisation process conditions.

The resulting metallocene containing polymer may be reacted with an olefin to produce a polyolefin as described below. The polymer may be supported on an inorganic support as described above and may suitably be mixed with a co-catalyst.

The present invention also provides a process for the production of polyolefins, in particular homopolymers of ethylene and copolymers of ethylene with minor amounts of at least one C3 to C8 alpha-olefin. The process comprises contacting the monomer or monomers, optionally in the presence of hydrogen, with a catalyst composition comprising at least one metallocene complex of formula I or II in an olefin polymerisation catalyst composition according to the above aspects of the present invention at a temperature and pressure sufficient to initiate the polymerisation reaction. The catalyst composition may preferably be in the form of a supported metallocene containing polymer of the metallocene complex as described above.

Suitably the alpha olefin may be propylene, butene-1, hexene-1, 4-methyl pentene-1 and octene-1 and may be present with the ethylene in amounts of 0.001–80% by weight (of the total monomers). The polymers or copolymers of ethylene thus obtained can have densities, in the case of homopolymers of about 950 to 960 or 965 kg/m$^3$ or in the case of copolymers, as low as 915 kg/m3. The C3 to C8 alpha-olefin content in the copolymers of ethylene can be about from 0.01% to 10% by weight or more.

The olefin polymerisation catalyst compositions according to the present invention may be used to produce polymers using solution polymerisation, slurry polymerisation or gas phase polymerisation techniques. Methods and apparatus for effecting such polymerisation reactions are well known and described in, for example, Encyclopaedia of Polymer Science and Engineering published by John Wiley and Sons, 1987, Volume 7, pages 480 to 488 and 1988, Volume 12, pages 504 to 541. The catalyst according to the present invention can be used in similar amounts and under similar conditions to known olefin polymerisation catalysts.

The polymerisation may optionally be carried out in the presence of hydrogen. Hydrogen or other suitable chain transfer agents may be employed in the polymerisation to control the molecular weight of the produced polyolefin. The amount of hydrogen may be such that the percentage of the partial pressure of hydrogen to that of olefin(s) is from 0.01–200%, preferably from 0.05–10%.

Typically, the temperature is from 30° to 110° C. for the slurry or "particle form" process or for the gas phase process. For the solution process the temperature is typically from 100° to 250° C. The pressure used can be selected from a relatively wide range of suitable pressures, e.g. from subatmospheric to about 350 MPa. Suitably, the pressure is from atmospheric to about 6.9 MPa, or may be from 0.05–10, especially 0.14 to 5.5 MPa. In the slurry or particle form process the process is suitably performed with a liquid inert diluent such as a saturated aliphatic hydrocarbon. Suitably the hydrocarbon is a C4 to C10 hydrocarbon, e.g. isobutane or an aromatic hydrocarbon liquid such as benzene, toluene or xylene. The polymer is recovered directly from the gas phase process or by filtration or evaporation from the slurry process or evaporation from the solution process.

Polymers having a broad range of density and melt indices as well as showing lower hexane extractables and excellent powder morphology and flowability may be obtained by using catalyst compositions according to the present invention. Film grade materials may be obtained having improved performance, and which show a very good balance between mechanical properties and processability.

Copolymers of ethylene with C3 to C8 alpha-olefins may be prepared in the form of porous powders having a melt index in the range 1–3 g/10 min, density in the range 0.910–0.925 g/cm³, a mean particle size in the range 400–1200 μm, a bulk density in the range 0.37–0.50 g/cm³ and a percentage of fines 125 μm of 0–1%.

Preferred copolymers are those obtained from C4 to C6 alpha-olefins having a melt index in the range 1.5–3 g/10 mm and density in the range 0.914–0.920 g/cm³.

Such copolymers are preferably prepared by copolymerisation in the gas phase.

The copolymers may be used to prepare both blown and cast films. For example blown films may be obtained of 25 μm thickness having an impact in the range 250 g (Method A)–700 g (Method B), secant modulus in the range 130–250 MPa, shear viscosity in the range 300–800 Pa.s. and hexane extractables on film of <2%. (by FDA 177.1520).

For catalyst compositions containing one metallocene complex, polymers of unimodal molecular weight distribution may be obtained. In the case where two or more metallocene complexes are present the resulting polymers may have bimodal or multimodal molecular weight distributions and, in the case of copolymerisation, have non-uniform branch distributions within the molecular weight distribution.

The catalyst compositions of the present invention which include metallocene containing polymer may also be used to prepare polyolefins having much lower melt indexes compared to those prepared using other metallocene catalysts.

Melt Index Measurement

The Melt Index (MI) of the polymers produced was determined according to ASTM D1238 Condition E, 2.16 kg at 190° C. while the High Load Melt Index (HLMI) was according to ASTM D1238 condition F, 21.6 kg at 190° C.

Method for Measuring the Molecular Weight Distribution

The molecular weight distribution of a (co)polymer is calculated according to the ratio of the weight-average molecular weight, Mw, to the number-average molecular weight distribution curve obtained by means of a "WATERS" (trademark) model "150 C" gel permeation chromatograph (High Temperature Size Exclusion Chromatograph), the operating conditions being the following:

solvent: 1,2,4-trichlorobenzene;
solvent flow rate: 1.0 ml/minute;
three "SHODEX" (trademark) model "AT 80 MS" columns of 25 cm length are employed;
temperature: 145° C.;
sample concentration: 0.1% by weight;
injection volume: 500 microlitres;
Universal standardisation using monodisperse polystyrene fractions.

The present invention will now be further illustrated with reference to the following examples:

All of the reactions and purifications detailed below involving organometallic species were carried out under a dry nitrogen atmosphere using standard vacuum-line techniques. Tetrahydrofuran and diethyl ether were dried over sodium benzophenone ketyl and distilled. Toluene was dried over sodium-potassium and distilled. Dichloromethane was dried over 4Å molecular sieves. All other reagents were used as received.

Impact Measurement

The impact measurement of polymer films was determined according to ASTM D1709-85. The test method determines the energy required to cause a polyethylene film to fail under specified conditions of impact of a free falling dart. The energy is expressed in terms of the weight. Two methods were used. In Method A the height used was 66 cms for films with impact resistances requiring masses <300 g and in Method B the height was 152.4 cm for films requiring masses >300 g.

Perforation Energy

The energy required to cause polyethylene film to perforate under specified conditions was determined according to ASTM D781 using an Adamel-Lhomargy puncture tester.

The present invention will be further illustrated with reference to the following examples.

EXAMPLE 1

Preparation of Bis(3-butenylcyclopentadienyl)zirconium Dichloride

Step (a) Preparation of 3-buten-1-tosylate

To a solution of 100 g (525 mmol) p-toluenesulphonyl chloride in 200 ml of dry pyridine cooled to 0° C. was added 21.1 g (29.3 mmol) 3-buten-1-ol. The reaction solution was thoroughly mixed and allowed to stand in a refrigerator at −5° C. overnight. The reaction mixture was then poured with stirring into 200 g of ice/water. The oily tosylate product was extracted from the aqueous mixture with 3×300 ml aliquots of ether. The combined ethereal fractions were washed twice with 300 ml of cold aqueous hydrochloric acid (conc HCl:water 1:1 w/w) to remove pyridine and then with 300 ml water, dried over potassium carbonate and sodium sulphate and decolourised with activated carbon. The suspension was filtered and the ether evaporated from the filtrate under reduced pressure to leave a pale yellow oil. The oil was then washed with cold pentane to remove impurities and induce crystallisation. 51.0 g of spectroscopically pure product ($^1$H NMR) as a microcrystalline white solid were isolated (225 mmol, 76.7%).

Step (b) Preparation of 3-butenylcyclopentadiene

To a solution of 25.0 g (110 mmol) 3-buten-1-tosylate prepared according to step (a) above in 200 ml THF cooled to 0° C. was added 68.9 ml of 2.0M (138 mmol) sodium cyclopentadienylide in THF. The reaction mixture was allowed to warm to room temperature and was stirred for 16 h. 100 ml concentrated aqueous saline solution was added and the product extracted with ether (3×75 ml). The combined organic fractions were dried over magnesium sulphate for 2 hours, filtered and the solvents removed under reduced pressure using a rotary evaporator to yield a dark brown oil. The crude product was distilled under reduced pressure (b.p. 50°–51° C. @ 15 mm Hg) to give 5.71 g of a colourless oil (47.6 mmol, 43.3%).

Step (c) Preparation of Bis(3-butenylcyclopentadienyl) zirconium Dichloride 19 ml of 2.5M (47.5 mmol) butyllithium in mixed $C_6$ alkane solvent was slowly added to 5.7 g (47.5 mmol) 3-butenylcyclopentadiene prepared according to step (b) above in 50 ml THF cooled to 0° C. and stirred for 1 hour. The lithium 3-butenyl cyclopentadienylide solution produced was added to 4.43 g (19.0 mmol) zirconium tetrachloride in 50 ml THF cooled to 0° C. and stirred for 65 hours. The volatiles were removed under vacuum and the residue extracted with ether and filtered. The product was precipitated as a microcrystalline white solid upon slow cooling of the solution to −50° C. Recrystallisation from cold ether (−12° C.) yielded 1.54 g of spectroscopically pure product ($^1$H NMR) as colourless needles (3.85 mmol, 20.2%).

EXAMPLE 2

Preparation of Bis(3-propenylcyclopentadienyl)zirconium Dichloride

Step (a) Preparation of 3-Propenylcyclopentadiene

To a rapidly stirred solution of allylbromide (42.73 g; 0.35 mol) dissolved in dry THF (200 ml) at 0° C. was added a solution of sodium cyclopentadiene (220 ml, 2.0M; 0.44 mol) in THF. The reaction was stirred for 2 hrs during which time it was allowed to warm to room temperature. Iced water (1500 ml) was added and the organic product extracted with diethyl ether (3×400 ml). The combined organic fractions were dried over magnesium sulphate overnight, filtered and the solvents removed under reduced pressure using a rotary evaporator to yield a pale brown oil. The crude product was distilled under reduced pressure (b.p. 35–45° C. @ 17 mm Hg) to give 11.17 g of a colourless oil (0.105 mol, 33.3%).

Step (b) Preparation of bis (3-propenylcyclopentadienyl) zirconium Dichloride

Methyllithium solution (75.25 ml, 1.4M; 0.105 mol) in diethyl ether was slowly added to a rapidly stirred solution of propenylcyclopentadiene (11.17 g, 0.105 mol) in dry diethyl ether at 0° C. The reaction was warmed to room temperature and stirring continued until gas evolution had ceased. The precipitated lithium propenylcyclopentadienylide was isolated by filtration, washed with diethyl ether (2×100 ml) and pumped to dryness to give 10.65 g (0.095 mol) of fine white powder. To a rapidly stirred THF solution (100 ml) of the lithium propenylcyclopentadienylide at 0° C. was added zirconium tetrachloride (11.09 g, 47.5 mmol) dissolved in dry THF (100 ml). The reaction mixture was allowed to warm to room temperature and was stirred for 16 hrs. The volatiles were removed under vacuum and the residue extracted with diethyl ether (4×100 ml) and filtered. The product was obtained as a microcrystalline white solid upon slow cooling of the solution to −78° C. Recrystallisation from cold ether yielded 13.33 g of spectroscopically pure product ($^1$H NMR) as colourless needles (35.8 mmol, 75.4%).

EXAMPLE 3

Preparation of Supported Catalyst 15 mol of MAO (10% solution in toluene, WITCO) and 100 mmol bis(3-propenylcyclopentadienyl)zirconium dichloride (prepared as in Example 2) in 1.5 liters toluene were maintained at room temperature with stirring for 15 min. 2 kg of silica (GRACE SD 3217.50 dried at 800° C. for 5 hrs) was added to the mixture to form a suspension. The resultant mixture was stirred for 1 hr at room temperature, the suspension transferred to a drier and the solvent removed at 120° C. to provide a free-flowing spherical powder.

EXAMPLES 4–5

Preparation of Supported Catalysts

The procedure in Example 3 was repeated using bis(3-butenylcyclopentadienyl)zirconium dichloride (prepared as in Example 1) and Crosfield ES70 silica in Example 4 and Grace SD 3217.50 silica in Example 5.

EXAMPLE 6

Ethylene homopolymerisation 400 g sodium chloride were introduced under nitrogen into a 2.5 liter stainless steel autoclave equipped with a stirrer. The temperature was increased to 80° C. and the autoclave charged with supported catalyst obtained in Example 3 (0.02 mmol Zr). Ethylene pressure was increased to 0.8 MPa. After 2 hrs the sodium chloride was removed by washing with water to yield 245 g polyethylene of very good morphology having a melt index of 0.8 g/10 min measured at 190° C. under a load of 2.16 kg (ASTM-D-1238-condition E), bulk density 0.42 g/cm$^3$, an average particle diameter measured by laser diffraction of 545 µm and 0.6% of fine powder less than 125 µm.

EXAMPLE 7

Ethylene/1-butene copolymerisation

The procedure of Example 6 was repeated using supported catalyst (0.025 mmol Zr), an ethylene pressure of 0.9 MPa and the introduction of 1-butene into the autoclave to produce a polymer of density of 0.920 g/cm$^3$ non annealed. After 70 min. the sodium chloride was removed by washing with water to yield 575 g of copolymer of very good morphology containing 4.8 wt % of butene, having a melt index of 3 g/10 min. measured at 190° C. under a load of 2.16 kg, 0.6% Kumagawa $C_6$-extractables and bulk density 0.43 g/cm$^3$.

EXAMPLE 8

Ethylene/1-butene copolymerisation

The procedure in Example 7 was repeated using supported catalyst as described in Example 4 (0.1 mmol Zr) and an ethylene pressure of 0.25 MPa. 1-Butene was introduced to give a polymer of density of 0.916 g/cm$^3$ non annealed. After 2 hrs the sodium chloride was removed to yield 530 g of copolymer of very good morphology having a melt index of 7.8 g/10 min measured at 190° C. under a load of 2.16 kg, 2% Kumagawa $C_6$ extractables and a bulk density of 0.44g/cm$^3$.

The comonomer was very well distributed in the polymer showing a relative dispersity measured by $^{13}$C NMR (Brucker, 200 MH$_z$) of 103.3 and branching dispersity measured by differential scanning calorimetry (after storing at 200° C., cooling at a rate of 16° C. per minute and heating at a rate of 16° C. per minute) after flow cooling in the range 1.3 to 1.5.

EXAMPLE 9

Ethylene homopolymerisation

The procedure was carried out in a fluidised bed reactor having a diameter of 15 cm, height of 1 m and operating with the aid of a fluidisation gas propelled at an upward velocity of 25 cm/s. Ethylene pressure was maintained at 1 MPa, hydrogen maintained during 2 hrs 35 min. at a ratio of PH$_2$/PC$_2$=0.004 and the temperature maintained at 90° C. 1000 g of anhydrous homopolyethylene was introduced as a charge powder followed by catalyst of Example 5 (0.18 mmol Zr). 4630 g polyethylene was obtained having a melt index of 3.7 g/10 measured at 190° C. under a load of 2.16 kg, density of 0.961 g/cm3 non annealed and a bulk density of 0.36 g/cm3.

EXAMPLE 10

Ethylene/1-butene copolymerisation

The procedure in Example 9 was repeated using an ethylene pressure of 1.15 MPa while 1-butene was maintained for 3 hrs at a ratio of PC$_4$/PC$_2$=0.042 at a temperature of 55° C. Supported catalyst of Example 5 (0.07 mmol Zr) was used to yield a copolymer having a melt index of 1.2 g/10 min measured at 190° C. under a load of 2.16 kg, a density of 0.913 g/cm$^3$, a bulk density of 0.41 g/cm$^3$ and 0.6% Kumagawa C$_6$ extractables.

EXAMPLE 11

Ethylene/n-hexene copolymerisation

Ethylene, n-hexene and nitrogen were fed into a continuous fluidised bed reactor of diameter 45 cms maintained at a total pressure of 1.9 MPa. The gas composition was maintained constant at PC$_6$/PC$_2$=0.03 and supported catalyst of Example 3 injected into the reactor continuously at a rate of 7 g/hr to maintain a constant reaction rate in the reactor. Polymer product was continuously removed from the reactor through a valve as copolymer of density of 0.916 g/cm$^3$ non annealed having 1 ppm of catalyst residues and 560 Pa.s of shear viscosity at 100 radian/s.

The reaction conditions were varied to prepare different types of copolymer which all exhibit very high impact strength combined with excellent processability. The results are given in Table 1.

EXAMPLE 12 (Comparative)

A mixture of 150 mmol MAO (WITCO) and bis(n-butylcyclopentadienyl)zirconium dichloride in 50 ml of toluene were stirred at room temperature under nitrogen. 20 g silica (Grace SD 3217.50, dried at 800° C. for 5 hr) were added to the mixture to form a suspension and the mixture stirred for 1 hr at room temperature before raising the temperature to 120° C. and the solvent removed to give a free flowing powder.

EXAMPLE 13 (Comparative)

400 g of sodium chloride were introduced into a 2.5 liter stainless steel autoclave equipped with a stirrer. The temperature was increased to 80° C. and the autoclave charged with the supported catalyst obtained in Example 12 (0.1 mmol Zr). Ethylene pressure was increased to 0.2 MPa and after 5 hrs the sodium chloride removed by washing with water to yield polyethylene having a melt index of 7.7 g/10 min measured at 190° C. under a load of 2.16 kg (ASTM-D-1238 Condition-E), an average particle diameter measured by laser diffraction of 376 µm and 7.5% of fine powder less than 125 µm.

EXAMPLES 14–16

Preparation of Metallocene-containing Polymers

Preparative details for each polymer, and the zirconium content before and after toluene washing, are given in Table 2.

A solution of MAO in toluene was added to the metallocene complex and the solution stirred to dissolve the metallocene. The mixture was heated to 50° C. and ethylene introduced at a measured flow rate. After the ethylene flow was stopped the mixture was filtered and the solid polymer washed with 5×25 ml aliquots of toluene at room temperature. Residual solvent was removed under vacuum.

A sample of each metallocene containing polymer (0.5–1 g) was transferred to a round bottom flask, 100 ml toluene added and the mixture stirred while the flask was heated to 100° C. for 3 hrs resulting in a clear pale yellow solution. The flask was cooled to room temperature resulting in reprecipitation of the polymer. The solution was filtered and the polymer washed with 5×25 ml aliquots of toluene at room temperature. Residual solvent was removed under vacuum.

Due to the high solubility of the free metallocene complex in toluene, the zirconium analyses before and after washing indicate that the metallocene complex has been incorporated into the polymer.

EXAMPLE 17

Preparation of Supported Metallocene-containing Polymer 750 mmol (Al) MAO (WITCO, 10% in toluene), and 5 mmol of bis(3-butenylcyclopentadienyl)zirconium dichloride (prepared as in Example 1) in 200 ml toluene were added under N$_2$ to 1.3 liters of toluene at 80° C. in a stainless steel reactor. Ethylene was introduced into the reactor at a uniform rate of 100 g/h for 30 min. and then the reactor cooled to 20° C. and the contents washed several times with cold toluene. No Zr was detected in the toluene washings. The toluene was removed under vacuum and 10 g of the resultant product extracted under N$_2$ with boiling toluene in the presence of 20 g of silica SD 3217.50 in the recovery flask. The content of the flask was transferred to a rotatory drier and the solvent removed to yield the free flowing catalyst.

EXAMPLE 18

Ethylene homopolymerisation 6.8 g of the supported metallocene containing polymer prepared in Example 17 (0.078 mmol Zr) was premixed with 36 mmol of Al as MAO (WITCO, 10% in toluene) and the toluene removed under vacuum. 400 g of sodium chloride were introduced under N$_2$ into a 2.5 liter stainless steel autoclave, the temperature increased to 80° C. and the autoclave charged with the supported catalyst. Ethylene pressure was increased to 0.2 MPa and after 5 hrs the sodium chloride was removed by washing with water to yield 420 g of polyethylene having a melt index of 0.7 g/10 min measured at 190° C. under a load of 2.16 kg (ASTM-D-1238 Condition E) and a bulk density of 0.42 g/cm$^3$.

By using a supported metallocene containing polymer a much lower melt index was achieved when compared with other metallocene catalysts as shown by comparative Example 13.

EXAMPLE 19

Preparation of Supported Metallocene-containing Polymer

Metallocene containing polymer prepared according to Example 14 (0.27 g) was dissolved in 15 ml toluene at 80° C. and added to 1.73 g Crosfield ES70 silica (precalcined in flowing N$_2$ at 500° C. for 4 hrs) with stirring. The solvent was removed in vacuum while maintaining the temperature at 80° C. to yield a white, free flowing powder having 0.12% w/w Zr.

EXAMPLE 20

Ethylene polymerization 8.9 mmol of MAO (SCHERING, 30% in toluene) in 10 ml toluene were added to 1.2 g of supported catalyst prepared as in Example 19 with stirring at 25° C. for 90 min. The solvent was removed under vacuum at 25° C. to leave a free flowing powder containing 0.084% w/w Zr. 0.55 g (5.07×10-3 mmol Zr) of the powder was added to a 3 liter stirred gas phase polymerisation reactor. No further addition of MAO cocatalyst was made. Ethylene (0.8 MPa) was introduced at 75° C. and the flow allowed to maintain constant reactor pressure. After 2 hrs the pressure was reduced rapidly and the reaction quenched using 2-propanol to yield 30g of polyethylene having Mw of 228,000, Mw/Mn of 2.6 and 370 g PE/mmol Zr.h.b.

TABLE 1

| Density g/cm$^3$ | MI g/10 min | Impact g | Perforation Energy (dj) | Output/pressure* kg/h.b. | Thickness μm | Secant Modulus** MPa |
|---|---|---|---|---|---|---|
| 0.914 | 2.9 | 550 (B) | 94 | 0.25 | 25 | 131 |
| 0.916 | 2.3 | 533 (B) | 67 | 0.25 | 38 | 132 |
| 0.918 | 2.8 | 271 (A) | 35 | 0.24 | 25 | 169 |

*measured on Kiefel/R040 (die diameter 100 mm, die gap 1.2 mm)
**by ASTM D882-88

TABLE 2

| Example | Metallocene | Quantity/mmol | MAO/mmol | Solvent/ml | C$_2$ flow Rate/ml/min | Reaction Time/h | Polymer Yield/g | Zr Content/% Before Washing | Zr Content/% After Washing |
|---|---|---|---|---|---|---|---|---|---|
| 14 | Propenylzirconium Dichloride | 4 | 240 | 40 | 33 | 6.17 | 9 | 0.87 | 0.76 |
| 15 | Propenylzirconium Dichloride | 4 | 240 | 40 | 6.5 | 21.17 | 4.4 | 0.70 | 0.70 |
| 16 | Propenylzirconium Dichloride | 4 | 240 | 40 | 30 | 6 | 9.8 | 0.68 | 0.74 |

We claim:

1. A catalyst for use in the polymerisation of olefins characterised in that it comprises at least one metallocene complex of general formula I or II

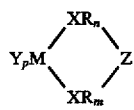
(II)

wherein R is a monovalent or divalent 1–20C hydrocarbyl group, or a 1–20C hydrocarbyl group containing substituent oxygen, silicon, phosphorus, nitrogen or boron atoms, with the proviso that at least one R group contains a polymerizable olefinic group containing up to 4 carbon atoms, and, when there are two R groups present, they may be the same or different, and when R is divalent it is directly attached to M, and replaces a Y ligand,
wherein X is cyclopentadienyl or indenyl M is a Group IVA metal, Y is a monovalent anionic ligand, and for formula I, n is an integer of 1 to 10 x is either 1 or 2, and when x=1, p=0–3, when x=2, p=0–2, and for formula II, n and m are integers or 0 such that n+m≥1, p=0–2, and z is a C$_1$ to C$_4$ alkylene radical or a dialkyl germanium or silicon or an alkyl phosphine or amine radical or bis-dialkylsilyl or dialkylgermanyl containing hydrocarbyl groups having 1 to 4 carbon atoms bridging said cyclopentadienyl or indenyl group.

2. A catalyst according to claim 1 wherein M in general formula I or II is zirconium.

3. A catalyst according to claim 1 wherein the olefinic group is a vinyl group.

4. A catalyst according to claim 1 wherein the metallocene complex is supported on an inorganic support.

5. A catalyst according to claim 4 wherein the inorganic support is selected from silica, alumina and Group IIA metal halides.

6. A catalyst for use in the polymerisation of olefins comprising at least one polymer of at least one metallocene complex of general formula I or II as described in claim 1 and at least one olefins.

7. A catalyst according to claim 6 wherein the polymer is supported on an inorganic support.

8. A catalyst according to claims 1 or 6 further comprising a cocatalyst.

9. A catalyst according to claim 8 in which the cocatalyst is an organo aluminium compound.

10. A catalyst as defined in claim 1 wherein X is cyclopentadienyl nucleus.

11. A catalyst as defined in claim 1 wherein the polymerizable olefinic group is propene or butene.

12. A catalyst as defined in formula I of claim 1.

13. A catalyst as defined in claim 1 wherein X is a cyclopentadienyl nucleus and the polymerizable olefinic group is propene or butene.

14. Bis(3-butenylcyclopentadienyl)zirconium dichloride.

15. Bis(3-propenylcyclopentadienyl)zirconium dichloride.

* * * * *

UNITED STATES PATENT AND TRADEMARK OFFICE
CERTIFICATE OF CORRECTION

PATENT NO. : 5,714,425
DATED : February 3, 1998
INVENTOR(S) : CHRISTINE J. CHABRAND ET AL It is certified that error appears in the above-identified patent and that said Letters Patent is hereby corrected as shown below:

Column 1, as line 29, insert:
-- $M[XR_n]_x Y_p$      (I) --

Claim 1, as line 4, insert:
-- $M[XR_n]_x Y_p$      (I) --

Claim 6, last line, change "olefins" to --olefin--.

Signed and Sealed this

Thirtieth Day of June, 1998

Attest:

BRUCE LEHMAN

*Attesting Officer*      *Commissioner of Patents and Trademarks*